(12) United States Patent
Ikemoto et al.

(10) Patent No.: US 9,174,983 B2
(45) Date of Patent: Nov. 3, 2015

(54) PYRROLOQUINOLINE QUINONE DISODIUM SALT CRYSTAL AND METHOD FOR PRODUCING THE SAME

(75) Inventors: Kazuto Ikemoto, Niigata (JP); Hitoshi Sakamoto, Tsukuba (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/125,788

(22) PCT Filed: Jun. 15, 2012

(86) PCT No.: PCT/JP2012/065303
§ 371 (c)(1),
(2), (4) Date: Jan. 9, 2014

(87) PCT Pub. No.: WO2012/173217
PCT Pub. Date: Dec. 20, 2012

(65) Prior Publication Data
US 2014/0128609 A1 May 8, 2014

(30) Foreign Application Priority Data
Jun. 16, 2011 (JP) ................................. 2011-134279

(51) Int. Cl.
*C07D 471/04* (2006.01)
*C12P 7/66* (2006.01)

(52) U.S. Cl.
CPC ................. *C07D 471/04* (2013.10); *C12P 7/66* (2013.01)

(58) Field of Classification Search
CPC ....... C07D 471/04; C12P 7/66; A61K 31/475
See application file for complete search history.

(56) References Cited

U.S. PATENT DOCUMENTS

| 2003/0216424 A1 | 11/2003 | Davis |
| 2012/0116087 A1 | 5/2012 | Edahiro et al. |

FOREIGN PATENT DOCUMENTS

| EP | 2 455 379 A1 | 5/2012 |
| JP | 62-246575 | 10/1987 |
| JP | 2-67284 | 3/1990 |
| JP | 7-113024 | 12/1995 |
| JP | 2005-530786 | 10/2005 |
| JP | 2007-269769 | 10/2007 |
| JP | 2011-98911 | 5/2011 |
| JP | 2011-246442 | 12/2011 |
| WO | WO 03/097056 A1 | 11/2003 |
| WO | WO 2011/007633 A1 | 1/2011 |
| WO | WO 2011/055796 A1 | 5/2011 |

OTHER PUBLICATIONS

2003 Brief Communications, Takaoki Kasahara et al. A new Redox co-factor vitamin for mammals.*
Davidovich M et al. Detection of Polymorphism by powder X-ray Diffraction: Interference by preferred Orientation. , 2004.*
International Prliminary Report on Patentability (Chapter 1) with Written Opinion issued on Jan. 3, 2014 in PCT/JP2012/065303 (English Translation only).
International Search Report issued Sep. 11, 2012, in PCT/JP12/065303 filed Jun. 15, 2012.
Ishida, et al., "Molecular and Crystal Structure of PQQ (Methoxatin), a Novel Coenzyme of Quinoproteins: Extensive Stacking Character and Metal Ion Interaction", J. Am. Chem. Soc., vol. 111, 1989, pp. 6822-6828.
Kazuto Ikemoto, et al., "Crystal structure and characterization of pyrroloquinoline quinone disodium trihydrate", Chemistry Central Journal, vol. 6, No. 1, 57, XP 021137638, (Jun. 19, 2012), pp. 1-7.

* cited by examiner

*Primary Examiner* — Rita Desai
(74) *Attorney, Agent, or Firm* — Oblon, McClelland, Maier & Neustadt, L.L.P.

(57) ABSTRACT

An object of the present invention is to provide a novel pyrroloquinoline quinone disodium crystal having excellent dispersibility in solvents and excellent permeability through skin, and a method for producing the pyrroloquinoline quinone disodium crystal with high efficiency. According to the present invention, provided are a novel pyrroloquinoline quinone disodium crystal which is produced by drying a crystal produced under specified conditions through a drying means such as lyophilization, ambient drying and vacuum drying, and a method for producing the pyrroloquinoline quinone disodium crystal.

7 Claims, 3 Drawing Sheets

US 9,174,983 B2

PYRROLOQUINOLINE QUINONE DISODIUM SALT CRYSTAL AND METHOD FOR PRODUCING THE SAME

CROSS-REFERENCE TO RELATED APPLICATION

This application enjoys the benefit of priority to earlier Japanese Patent Application No. 2011-134279 filed on Jun. 16, 2011, the disclosure of which is incorporated herein by reference in its entirety.

FIELD OF THE INVENTION

This invention relates to a disodium salt crystal of pyrroloquinoline quinone and a method for producing the same.

BACKGROUND OF THE INVENTION

Pyrroloquinoline quinone (hereinafter sometimes referred to as "PQQ") has been proposed as a possible new vitamin (see, for example, Non-patent document 1). Moreover, PQQ is present not only in bacteria but also in eukaryotic molds and yeasts and plays an important role as a coenzyme. Also, PQQ has been found to have many physiological activities such as cell growth-promoting activity, anti-cataract activity, hepatic disease-preventing and therapeutic activity, wound healing activity, anti-allergic activity, reverse transcriptase-inhibiting activity, glyoxalase I-inhibiting activity and anticancer activity, and the like. PQQ has thus attracted much attention as a useful material in the fields of pharmaceuticals, foods, and cosmetics. In the field of pharmaceuticals, PQQ is expected to be applied as therapeutics for cardiac diseases (Patent Document 1), dermatoses (Patent Document 2), and neurodegenerative diseases (Patent Document 3), for example. PQQ is also expected to be applied as a substance that has an anti-aging effect in the field of foods and that has a skin-beautifying effect in the field of cosmetics.

PQQ can be produced by methodologies such as organic chemical syntheses and fermentation processes and is often provided in the form of an alkali metal salt crystal, in particular a disodium salt crystal (hereinafter sometimes referred to as "disodium crystal"). The PQQ disodium crystal is in the crystalline pentahydrate form, and single crystal analysis has revealed the structure of the disodium crystal (Non Patent Document 1). In addition to the method described in Non Patent Document 1, reported methods for producing the PQQ disodium crystal include pH adjustment of a solution of PQQ disodium to crystallize PQQ disodium (Patent Document 4) and precipitation using an aqueous organic solvent to precipitate the PQQ disodium crystal from the aqueous solution (Patent Document 5). Any of these methods, however, produces a solid having a low degree of crystallinity or uses an inedible solvent. In addition, the crystal produced does not always have a high preservability.

When applied to pharmaceuticals and cosmetics, PQQ is desired to have a high degree of crystallinity, contain few impurities, have a stable solubility or a high dispersibility in a solvent, and have a high degree of preservability. When applied to foods and pharmaceuticals, PQQ is also desired to be harmless to the human body. When applied to skin pharmaceuticals and cosmetics, PQQ is further desired to have a high degree of permeability through the skin.

PRIOR ART DOCUMENTS

Patent Document

[Patent document 1] Japanese Unexamined Patent Application publication No. 2005-530786
[Patent document 2] Japanese Unexamined Patent Application publication No. 2011-246442
[Patent document 3] Japanese Unexamined Patent Application publication No. 2007-269769
[Patent document 4] WO 2011/007633
[Patent document 5] Japanese Examined Patent Application publication No. H07-113024

Non-Patent Document

[Non-patent document 1] Ishida, T. Et al., "Molecular and crystal structure of PQQ(methoxatin), a novel coenzyme of quinoproteins: extensive stacking character and metal ion interaction", Journal of American Chemical Society, 1989, Vol. 111, p. 6822-6828.

SUMMARY OF THE INVENTION

Subject to be Solved by the Invention

An object of the present invention is to provide a novel PQQ disodium crystal having excellent dispersibility in a solvent and excellent permeability through the skin and useful in the fields of pharmaceuticals, cosmetics or foods, and a method for producing the same with high efficiency.

Solution to Problem

The present inventors have found that a PQQ disodium crystal can be prepared under specified conditions to produce the PQQ disodium crystal in novel crystalline forms (Crystalline Form 1 and Crystalline Form 2). Specifically, the present inventors have found that a PQQ disodium crystal has heat stability in food oil, and have further found that when heated in food oil, a PQQ disodium crystal is provided in a good Crystalline Form 1 and Crystalline Form 2 in a short time. The present inventors have also found that the PQQ disodium crystal in Crystalline Form 1 and Crystalline Form 2 has a high degree of dispersibility in oils, and has a high degree of permeability through the skin. The present invention is based on these discoveries.

According to the present invention, the following inventions are provided:

(1) A pyrroloquinoline quinone disodium crystal having a water content of 7% by weight or less;
(2) The pyrroloquinoline quinone disodium crystal according to (1) having a water content of 4.6% by weight or less;
(3) The pyrroloquinoline quinone disodium crystal (Crystalline Form 1) according to (1) or (2), having 2θ angle peaks at 11.4±0.4, 13.5±0.4, 18.0±0.4, 18.7±0.4, 26.0±0.4, and 28.5±0.4° obtained by X-ray powder diffraction using a Cu Kα radiation;
(4) The pyrroloquinoline quinone disodium crystal (Crystalline Form 2) according to (1) or (2), having 2θ angle peaks at 8.7±0.4, 11.5±0.4, 12.0±0.4, 17.4±0.4, and 18.7±0.4° obtained by X-ray powder diffraction using a Cu Kα radiation;
(5) A pharmaceutical composition comprising the pyrroloquinoline quinone disodium crystal according to any one of (1) to (4);
(6) A cosmetic composition comprising the pyrroloquinoline quinone disodium crystal according to any one of (1) to (4);
(7) A functional food or nutrient comprising the pyrroloquinoline quinone disodium crystal according to any one of (1) to (4);
(8) A method for producing the pyrroloquinoline quinone disodium crystal according to any one of (1) to (4), comprising the steps of producing a crystal that is a precursor of the pyrroloquinoline quinone disodium crystal (a precursor crystal) and then drying the precursor crystal;

(9) The method according to (8), wherein the precursor crystal is crystallized by adjusting the pH of an aqueous solution containing ethanol or isopropanol concentration of 10 to 90% in which a pyrroloquinoline quinone sodium salt is dissolved to pH between 2 to 5;

(10) The method according to (8) or (9), wherein the precursor crystal is a pyrroloquinoline quinone disodium crystal having 2θ angle peaks at 9.1±0.4, 10.3±0.4, 13.8±0.4, 17.7±0.4, 18.3±0.4, 24.0±0.4, 27.4±0.4, and 39.5±0.4° obtained by X-ray powder diffraction using a Cu Kα radiation;

(11) The method according to any one of (8) to (10), wherein the drying step is carried out by heating the crystal in an oil.

The PQQ disodium crystal according to the present invention not only has a high purity but also improves dispersibility in a solution and permeability through the skin, and is thus useful as an ingredient of cosmetics, pharmaceuticals or functional foods.

DETAILED DESCRIPTION OF THE INVENTION

Figure 1:
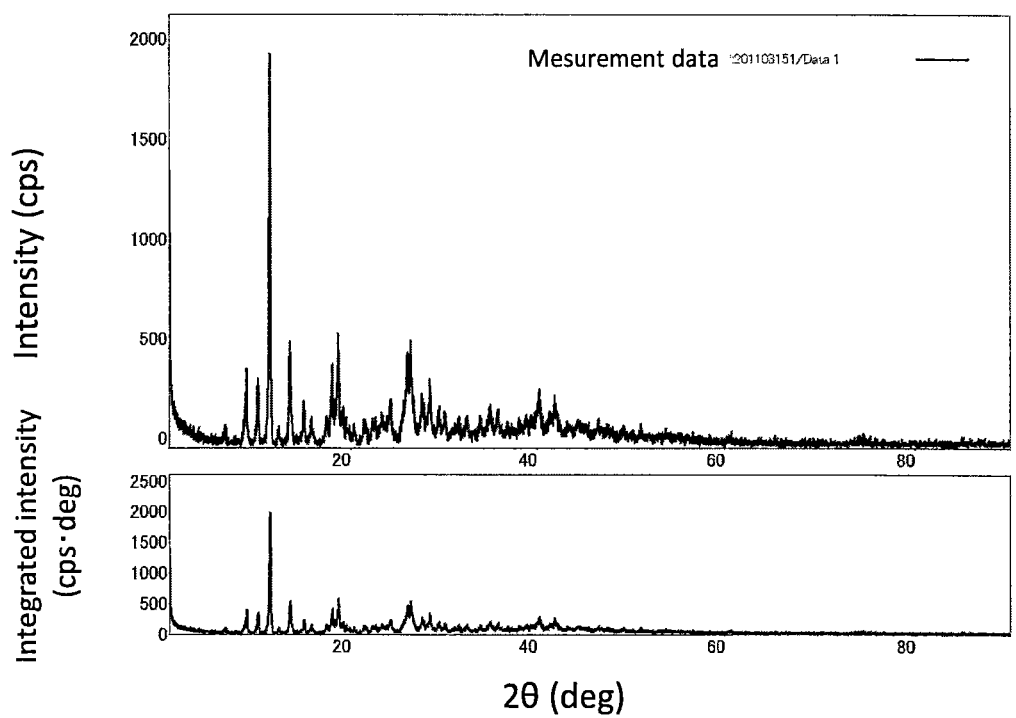
FIG. 1 shows the results of powder X-ray diffraction for a PQQ disodium crystal (Crystalline Form 1).

The PQQ disodium crystal according to the present invention has a low water content (hereinafter sometimes referred to as "low water content crystal"). Specifically, the PQQ disodium crystal according to the present invention has a water content of 7% or less, preferably of 4.6% or less, and more preferably of 3% or less. The PQQ disodium crystal according to the present invention is, for example, in Crystalline Form 1 or Crystalline Form 2 described in this specification, and may be a mixture of at least one crystal selected from crystals in Crystalline Form 1, Crystalline Form 2, and other crystalline forms. It is not particularly problematic in use that the PQQ disodium crystal in Crystalline Form 1 or Crystalline Form 2 according to the present invention may be mixed, for example, with a crystal that is a precursor of the PQQ disodium crystal according to the present invention (hereinafter sometimes referred to as simply "precursor crystal").

The PQQ disodium crystal according to the present invention is a PQQ disodium crystal (Crystalline Form 1) having 2θ angle peaks at 11.4±0.4, 13.5±0.4, 18.0±0.4, 18.7±0.4, 26.0±0.4, and 28.5±0.4° obtained by X-ray powder diffraction using a Cu Kα radiation. These peaks can be observed on a common X-ray powder diffractometer equipped with a monochromator. Since measured data also include a measurement error, the crystalline form defined by the present invention is a crystalline form that has the rational identity about the angle of the peaks.

The PQQ disodium crystal according to the present invention is preferably a PQQ disodium crystal (Crystalline Form 2) having 2θ angle peaks at 8.7±0.4, 11.5±0.4, 12.0±0.4, 17.4±0.4, and 18.7±0.4° obtained by X-ray powder diffraction using a Cu Kα radiation. In x-ray powder diffraction measurement, Crystalline Form 1 as a low water content crystal can be observed under the usual measurement conditions (at normal temperature), while Crystalline Form 2 cannot be observed in the usual humidity environment but is required to be measured in the environment of a high temperature state of 180° C. or more or in the dry atmosphere.

The PQQ disodium crystal according to the present invention is produced by a method comprising a step of producing a precursor crystal of the PQQ disodium crystal according to the present invention and drying the precursor crystal. The precursor crystal of a PQQ disodium crystal as used in the present invention refers to a PQQ disodium crystal having a water content of more than 4.6% and preferably more than 7%. In the present invention, the precursor crystal of a PQQ disodium crystal has preferably a water content of 14% or less.

As a starting material for the PQQ disodium crystal according to the present invention, a PQQ sodium salt (that is, a PQQ monosodium salt, a PQQ disodium salt and a PQQ trisodium salt) can be used, and preferred is PQQ trisodium. The PQQ sodium salt may contain sodium chloride as impurities which may be included during a production process, and these impurities can be suitably removed in the production process of the present invention to improve the purity of the product. The precursor crystal of a PQQ disodium salt crystal can be crystallized by adding a PQQ sodium salt (for example, a solid of PQQ sodium salt) in an aqueous solution having ethanol or isopropanol concentration of 10 to 90% by weight under the conditions where the solid of PQQ sodium salt does not dissolve completely (namely, conditions where the solution is saturated with PQQ sodium salt), and adjusting the pH of the solution to the range of 2 to 5 by adding an acid to the solution. The concentration of ethanol or isopropanol in the aqueous solution is preferably 35 to 65% by weight. The conditions where the PQQ sodium salt does not dissolve completely (namely, conditions where the solution is saturated with PQQ) vary depending on the concentration of an alcohol used. When a PQQ trisodium salt is used as a PQQ sodium salt, the concentration of the PQQ trisodium is 0.5 to 800 g/L, more preferably 0.5 to 100 g/L, and further more preferably 5 to 60 g/L. The higher concentration of the alcohol used allows the use of a solution having a lower concentration of PQQ in this process. Specifically, when the aqueous solution is a 50% ethanol aqueous solution, the concentration of PQQ trisodium to be used is 1 to 200 g/L. Also the pH of the aqueous solution can be adjusted more preferably to a range of 2.5 to 3.5.

The precursor crystal can be produced by adjusting the pH of the aqueous solution to a predetermined value followed by reaction for 0.1 to 96 hours. The reaction can be carried out for 6 to 72 hours for producing large crystals. Also, the reaction can be carried out at a temperature of 0 to 90° C., and more preferably 10 to 60° C. The conditions for crystallization can be freely selected in view of the effects of the presence and intensity of stirring on the quality of the crystal produced.

The resulting precursor crystal can be obtained by filtration, centrifugation, and decantation. This substance can be washed with an alcohol to be provided as a precursor crystal. Alternatively, the precipitated crystal can be provided as a precursor crystal as it is without such separating operations. The resulting precursor crystal is preferably a PQQ disodium crystal having 2θ angle peaks at 9.1±0.4, 10.3±0.4, 13.8±0.4, 17.7±0.4, 18.3±0.4, 24.0±0.4, 27.4±0.4, and 39.5±0.4° obtained by X-ray powder diffraction using a Cu Kα radiation, and preferably contains 12.7% water as water of crystallization.

In the production method according to the present invention, the precursor crystal of PQQ disodium crystal is crystallized followed by drying of the precursor crystal. This can result in the PQQ disodium crystal according to the present invention. Specifically, the precursor crystal can be dried by lyophilization, ambient drying or vacuum drying. In the drying step, adjustment of drying conditions such as drying time and drying temperature can promote the change in the crystalline form from the precursor crystal to the PQQ disodium crystal in Crystalline Form 1 or Crystalline Form 2 to yield the PQQ disodium crystal according to the present invention. The drying temperature varies depending on the method, and is, for example, −80 to 250° C., and preferably −60 to 250° C. The lower limit of the drying temperature is the starting temperature in the lyophilization, and the upper limit of the drying temperature is a temperature at which decomposition of the PQQ disodium does not occur. For example, the drying temperature can be −80 to 0° C., and preferably −60 to 0° C. in the lyophilization, 40 to 250° C. in ambient drying, and 0 to 250° C. in the vacuum drying. More specifically, for obtaining the PQQ disodium crystal in Crystalline Form 1, vacuum drying can be carried out, for example, by drying at 50° C. for 20 hours or more, and preferably 70 hours or more, and ambient drying can be carried out by heating at 120° C. or more and less than 180° C. for 30 minutes or more, without limitation. For obtaining the PQQ disodium crystal in Crystalline Form 2, ambient drying can be carried out, for example, at 180° C. or more for 30 minutes or more. Note that, the PQQ disodium in Crystalline Form 1 undergoes phase transition under atmospheric pressure at 180° C. to Crystalline Form 2. Therefore, the PQQ disodium in Crystalline Form 2 can be also produced by first preparing Crystalline Form 1, and then subjecting the crystal to phase transition. Moreover, the drying step can be stopped based on the water content in the crystal as an index. For example, the drying in the present invention can be stopped when the water content in the crystal as an index is 7% by weight or less, preferably 4.6% by weight or less, and more preferably 3% weight or less. The extent of decomposition of the PQQ disodium can vary depending on the surrounding environment, and the drying is preferably carried out in a nitrogen gas atmosphere compared with in a usual atmosphere from the viewpoint of reduction in decomposition. Also in a nitrogen gas atmosphere, the drying temperature can be higher than that in a usual atmosphere, whereby the drying time can be shortened.

In a more preferred embodiment of the method according to the present invention, the drying of the precursor crystal can be carried out by heating the precursor in an oil (for example, frying the precursor in an oil). When the precursor crystal is heated in an oil, from the viewpoint of progress of the change to Crystalline Form 1 or Crystalline Form 2, the heating temperature is preferably 120 to 200° C. under normal pressure. In order to obtain the PQQ disodium crystal in Crystalline Form 1, the oil temperature can be, but is not limited to, 120° C. or more and less than 180° C., for example, while in order to obtain the PQQ disodium crystal in Crystalline Form 2, the oil temperature can be higher, that is, 180 to 200° C. The heating temperature may exceed 200° C., unless the oil ignites or the PQQ disodium crystal decomposes. The heating time is preferably 30 minutes or more. Any edible oil can be used, including edible oils such as soybean oil, medium chain fatty acid oil, corn oil, fish oil, olive oil, rapeseed oil, rice bran oil, fish oil, and coconut oil. A mixture of an oil and PQQ disodium crystal obtained in this process may be used as it is as a slurry of the PQQ disodium crystal having a low water content, for example, for soft capsules, or may be used after removing the oil using hexane. So far, PQQ has been known for its high reactivity, but not for its heat stability in edible oils. According to the present invention, the PQQ disodium crystal has high-temperature stability, and is unexpectedly converted to a novel Crystalline Form 1 or Crystalline Form 2 by heating. Heating the precursor crystal in oils is advantageous in that the PQQ disodium crystal in Crystalline Form 1 or Crystalline Form 2 can be obtained in a short time.

The PQQ disodium crystal in Crystalline Form 1 and Crystalline Form 2 according to the present invention has a high degree of dispersibility in an edible oil, and has a high degree of permeability through skin. Moreover, the PQQ disodium crystal in Crystalline Form 1 and Crystalline Form 2 according to the present invention has a low water content, and may have a high degree of preservability. Further, the PQQ disodium crystal produced according to the present invention has an advantage of high purity because it is a crystal. In addition, the PQQ disodium crystal in Crystalline Form 2 is relatively hygroscopic in a humid atmosphere, and thus is preferably preserved in a dry atmosphere.

Accordingly, the PQQ disodium crystal according to the present invention can be suitably used as a food, functional food, nutrient, cosmetic, pharmaceutical or quasi-drug for human or animals. A functional food as used here means a food taken for the purpose of maintenance of health or nutrition as an alternative to a meal, such as a health food, nutritional supplement, food with nutrient function claims, and nutrient health food, and specified health food. The specific form for a food, functional food, nutrient, cosmetic, pharmaceutical or quasi-drug includes, but is not limited to, capsules (for example, a gelatin capsule, a soft capsule), tablets, chewables, tablets, and nutritious supplement drinks. The PQQ disodium crystal in Crystalline Form 1 and Crystalline Form 2 according to the present invention has a low water content, and thus is advantageous for tablet molding and preservation. As described above, the PQQ disodium crystal in Crystalline Form 1 and Crystalline Form 2 according to the present invention also has excellent dispersibility in oils and fats, and excellent permeability through the skin. Therefore, the present invention provides a pharmaceutical composition, a cosmetic composition, a functional food and a nutrient comprising the PQQ disodium crystal according to the present invention. Particularly, the crystal according to the present invention has excellent permeability through the skin, and thus the pharmaceutical composition of the present invention can be a pharmaceutical composition for percutaneous administration. Moreover, the crystal of the present invention has excellent dispersibility in oils and fats, and therefore is suitable for prescription for oil dispersion formulations. Therefore, the pharmaceutical composition and cosmetic composition according to the present invention may be provided in the form of a dispersion formulation like an emulsion or a suspension, the form of a semisolid formulation like an ointment or a cream, or the form of a formed formulation like a soft capsule.

When the PQQ disodium crystal according to the present invention is prepared as a functional food, an additive can be used including, for example, a sweetener, a colorant, a preservative, a thickening agent, an antioxidant, a color fixative, a bleaching agent, an antibacterial and antifungal agent, a gum base, a bittering agent, an enzyme, a glazing agent, an acidifier, a seasoning, an emulsifier, an enrichment, a manufacturing agent, a flavoring agent, and a spice extract. Also, the PQQ disodium crystal according to the present invention can be typically added to usual foods, for example, miso, soy sauce, instant miso soup, ramen, fried noodle, curry, corn soup, mapo dofu, mapo eggplant, pasta sauce, pudding, cake, and bread. Moreover, the pharmaceutical composition of the present invention may contain the PQQ disodium crystal according to the present invention and at least one formulation additive. The cosmetic composition of the present invention may contain the PQQ disodium crystal according to the present invention and at least one cosmetic additive. A person skilled in the art will suitably select the formulation additive and cosmetic additive according to the prescription form of the pharmaceutical composition and cosmetic composition, respectively.

EXAMPLES

The present invention will now be described in more detail with reference to the following reference Example, Examples and comparative Example, but is not intended to be limited thereto.

The X-ray powder diffraction measurement is carried out using M18XCE from Mac Science Co., Ltd. or RINT2500 from Rigaku Corporation, under the following conditions.
X-ray: Cu/tube voltage 40 kV/tube current 100 mA
Scanning rate: 4.000°/min
Sampling width: 0.020°
The water content (% by weight) of each crystal was determined by the Karl Fischer method.

Reference Example 1

Precursor Crystal

According to the description in the Japanese Patent No. 2751183, PQQ trisodium as a starting material was prepared by cultivation. The solid (60 g) of hydrous PQQ trisodium salt containing PQQ (20 g) was added to an aqueous solution (1 L) having an ethanol concentration of 50% by weight and the aqueous solution was saturated. At this time, the solid was not dissolved completely. The pH of the mixture was adjusted to 3.5 by adding hydrochloric acid to the mixture at room temperature. The hydrochloric acid was slowly added dropwise over about two hours. After the addition of hydrochloric acid, the mixture was stirred for two days, and then the resulting aqueous ethanol solution was filtered to prepare a hydrous PQQ disodium crystal (yield: 99 mol %). The X-ray powder diffraction measurement revealed that the resulting crystal had 2θ angle peaks at 9.1±0.4, 10.3±0.4, 13.8±0.4, 17.7±0.4, 18.3±0.4, 24.0±0.4, 27.4±0.4, and 39.5±0.4°. After the resulting crystal was disposed in an environment of a temperature of 40° C. and a relative humidity (RH) of 75%, the water content was measured. It was shown that the resulting crystal has a water content of 12.7% and has a purity of 87.3%.

Example 1

Crystalline Form 1

The precursor crystal prepared in Reference Example 1 was put in a vacuum dryer (Advantech Co., Ltd., Product name: FS-420), depressurized by a diaphragm type vacuum pump (DRYFAST ULTRA produced by A Gardner Denver, Product number: 2032) down to the limit of the device (2 Torr), and dried at 50° C. for 77 hours.

The X-ray powder diffraction measurement revealed that the resulting crystal was found to be a PQQ disodium crystal (Crystalline Form 1) having 2θ angle peaks at 11.4±0.4, 13.5±0.4, 18.0±0.4, 18.7±0.4, 26.0±0.4, and 28.5±0.4° (FIG. 1). As shown in FIG. 1, the PQQ disodium crystal prepared in this example was a crystal in a novel crystalline form (Crystalline Form 1) which is different from the crystalline form of the precursor crystal having a high water content. The water content measurement showed that the resulting crystal had a water content of 0.7%, and that the water content of the crystal was significantly reduced compared with that of the precursor crystal. The resulting crystal had a purity of 99.3%.

Example 2

Crystalline Form 1

The precursor crystal prepared in Reference Example 1 was put in a vacuum dryer (Advantech Co., Ltd., Product name: FS-420), and dried at atmospheric pressure at 120° C. for one day. The powder X-ray diffraction measurement revealed that the resulting crystal was found to be in a crystalline form identical to Crystalline Form 1 prepared in Example 1. The water content measurement showed that the resulting crystal had a water content of 2.2%, and a purity of 97.8%.

Example 3

Crystalline Form 1 (in Oil at 150° C. for 0.5 Hour)

The precursor crystal (9.6 g) prepared in Reference Example 1 was added to an edible oil ODO (65 g) made by Nisshin OilliO, and the mixture was heated (fried) at 150° C. for 30 minutes. The X-ray powder diffraction measurement revealed that the resulting crystal was found to be in a crystalline form identical to Crystalline Form 1 prepared in Example 1. Although the heating time was shorter than those of Examples 1 and 2, the precursor crystal was heated in oil to prepare Crystalline Form 1 in a short time.

The high performance liquid chromatography for the crystal prepared revealed that the amount of impurities contained in the crystal did not increase, and that the crystal prepared had a purity of 99% or more. The water content measurement showed that the resulting crystal had a water content of 1.9%. Although the heating time was shorter than those of Examples 1 and 2, the water content of the crystal prepared was significantly reduced, and was equivalent to the water content for Example 1 or 2.

Example 4

Crystal Mixture Having a Water Content of 7%

The precursor crystal prepared in Reference Example 1 was put in a vacuum dryer, was evacuated by a diaphragm type vacuum pump (DRYFAST ULTRA made by A Gardner Denver, Product number: 2032) down to the limit of the device (2 Torr), and was then dried at 50° C. for 22 hours.

The X-ray diffraction powder measurement revealed that the resulting crystal was found to be a mixture of the PQQ disodium crystal in Crystalline Form 1 having 2θ angle peaks at 11.4±0.4, 13.5±0.4, 18.0±0.4, 18.7±0.4, 26.0±0.4, and 28.5±0.4° and the precursor crystal obtained in Reference Example 1. The water content measurement showed that the resulting crystal had a water content of 7%, and had a purity of 93%. The resulting crystal mixture was then sequentially converted to the crystal in Crystalline Form 1 by reducing the water content (see, for example, Example 1 where the drying was conducted under the same conditions for 77 hours).

Example 5

Relationship Between the Heating Temperature and the Crystalline Form Prepared The relation between the heating temperature in the drying process and the crystalline form prepared was investigated in this example.

The precursor crystal prepared in Reference Example 1 was heated at a temperature change rate of 20° C./min, and the measurement was started 15 minutes after the temperature reached the respective preset temperatures. X-ray powder diffraction: 5 to 60°, 4°/min.

Figure 2:
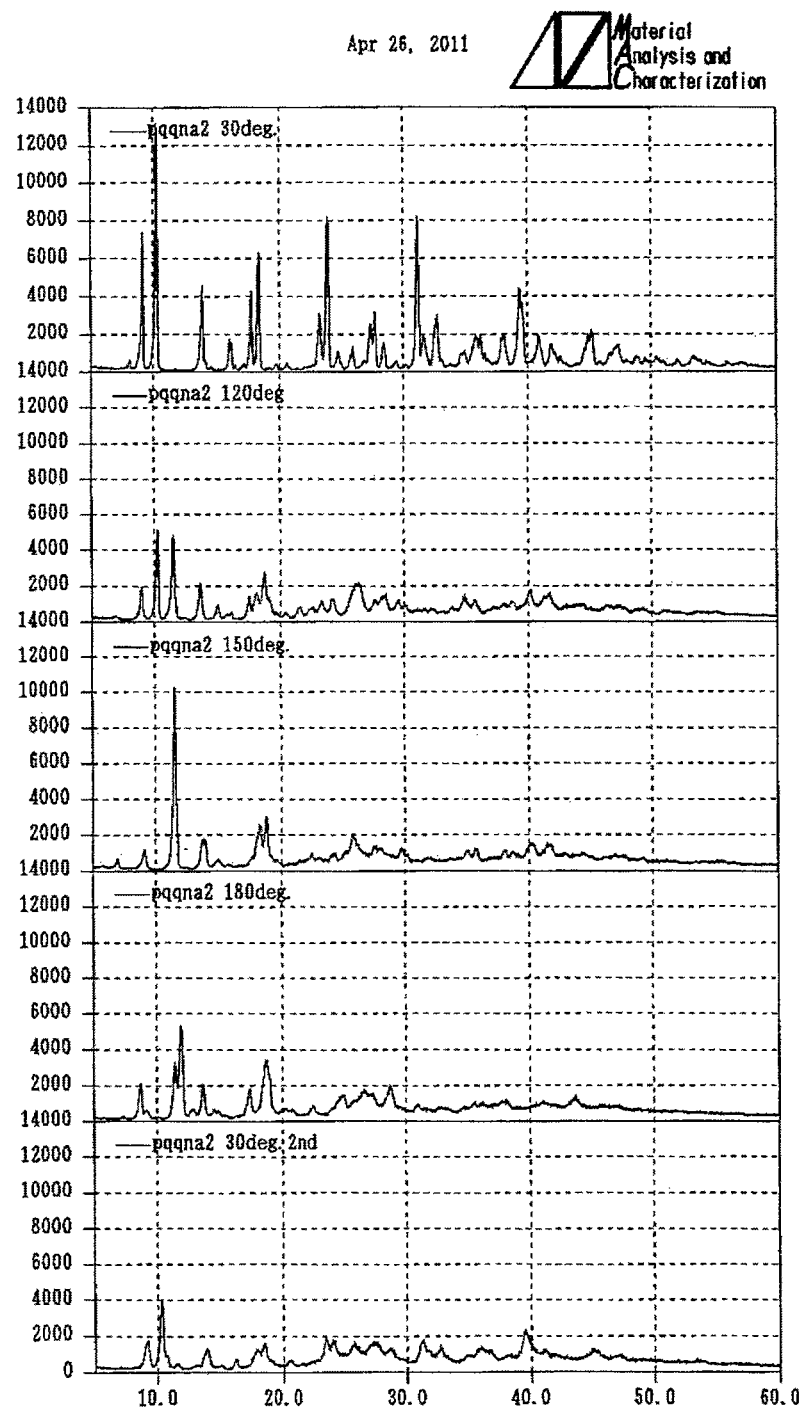
FIG. 2 shows the results of powder X-ray diffraction when the temperature in the drying step is changed.

The crystalline form of the crystal at each of the preset temperatures was investigated and it was shown that:
when the setting temperature was 30° C., the resulting crystal was similar to the precursor crystal;
when the setting temperature was 120° C., the resulting crystal was produced as a mixture of the precursor crystal and Crystalline Form 1, which is similar to the crystal mixture in Example 4 having a water content of 7%;
when the setting temperature was 150° C., the resulting crystal was a crystal in Crystalline Form 1; and
when the setting temperature was 180° C., the resulting crystals was a PQQ disodium crystal in a novel crystalline form (Crystalline Form 2) having 2θ angle peaks at 8.7±0.4, 11.5±0.4, 12.0±0.4, 17.4±0.4, and 18.7±0.4°. The results of the X-ray powder diffraction for the crystal treated at each temperature are shown in FIG. 2. The thermogravimetric analysis for the crystal in Crystalline Form 2 revealed that the water content of the crystal in Crystalline Form 2 was almost 0%. However, this crystal was unstable. When the crystal was allowed to stand still at 30° C. for a while (for example, a half day or more), it absorbed water and turned to a crystal in the crystalline form similar to that of the precursor crystal (FIG. 2).

Comparative Example 1

PQQ Disodium Crystal Different from Reference Example 1

Figure 3:
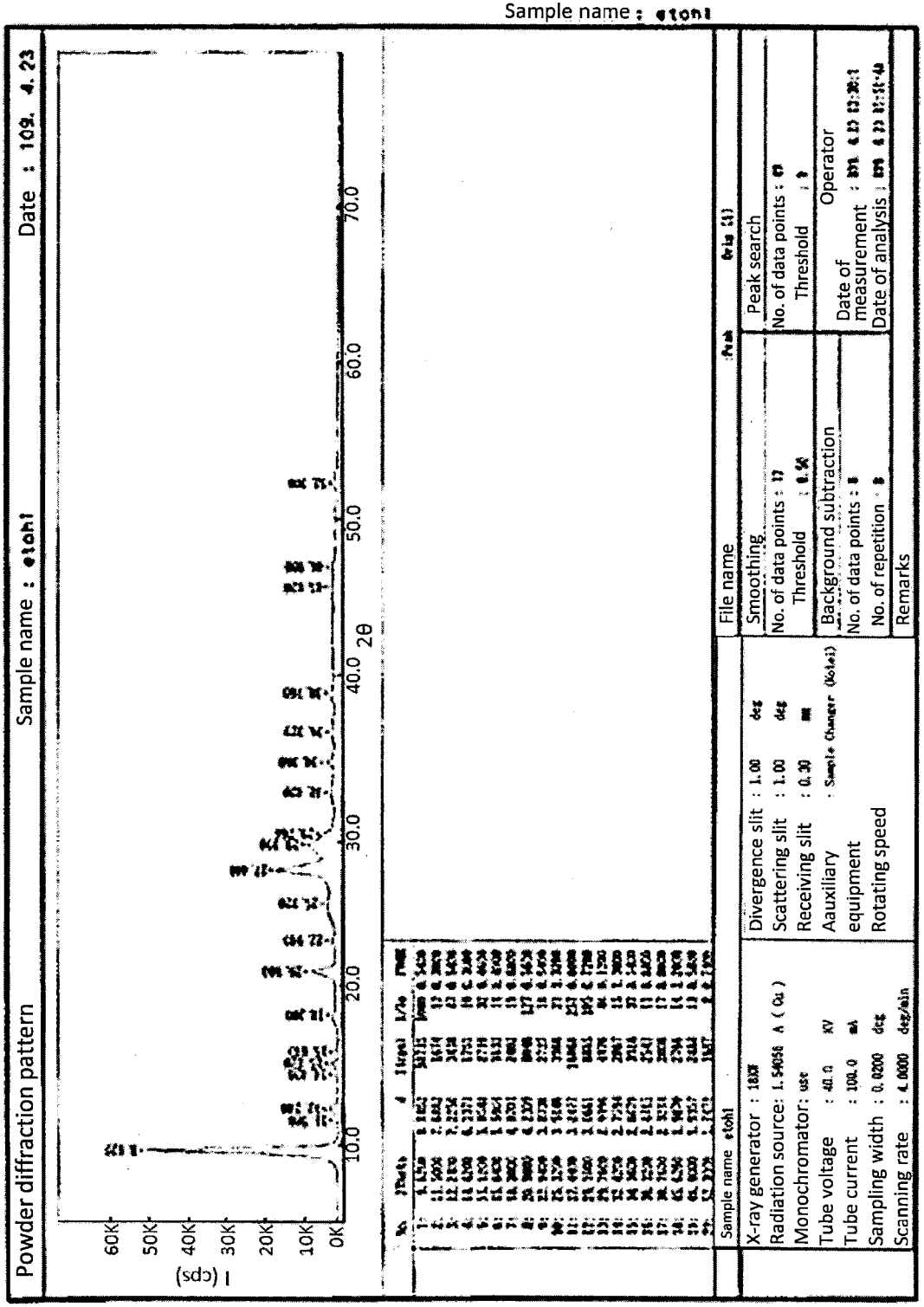
FIG. 3 shows the results of powder X-ray diffraction for the PQQ disodium crystal prepared by ethanol precipitation.

The precursor crystal in Reference Example 1 was dissolved in water, and ethanol was added to the solution to precipitate a red PQQ disodium crystal. The water content measurement showed that the resulting crystal had a water content of 14.5%. Subsequently, the resulting crystal was dried at a reduced pressure for 96 hours in a similar manner to Example 1 and subjected to an X-ray powder diffraction measurement. However, the crystal prepared by this method was found to have a structure having a low degree of crystallinity having 2θ angle peaks at 9.4 and 22.4° (FIG. 3). The water content measurement showed that the resulting crystal had a water content of 9.6%, and a purity of 90.4%.

Example 6

Dispersibility Test for PQQ Disodium Crystals in Crystalline Form 1 and Crystalline Form 2

In this example, the PQQ disodium crystal in Crystalline Form 1 and Crystalline Form 2 was compared in dispersibility in edible oils with the conventional crystals.

First, PQQ disodium crystals in Crystalline Form 1 and Crystalline Form 2 were prepared as follows: A crystal in Crystalline Form 1 was prepared by adding the precursor crystal (3 g) of the PQQ disodium salt obtained in Reference Example 1 to a glass vessel, evacuating by a diaphragm type vacuum pump (DRYFAST ULTRA made by A Gardner Denver, Product number: 2032) down to the limit of the device (2 Torr), and then drying at 150° C. for 4 hours at a reduced pressure to yield as a dark brown solid. After drying, the pressure in the vessel was returned to atmospheric pressure, and immediately the glass vessel was closed with a lid. A crystal in Crystalline Form 2 was prepared by adding the precursor crystal (3 g) of the PQQ disodium salt obtained in Reference Example 1 to a 200-mL eggplant-shaped flask, and heating at 200° C. for 4 hours under reflux with nitrogen gas at a flow rate of 100 mL/min to yield as a dark brown solid. After drying, the temperature within the flask was reduced to room temperature with nitrogen gas refluxed. In this example, the PQQ disodium crystal (precursor crystal) in Reference Example 1 was used as a control.

Each (5 mg) of the resulting crystals (the precursor crystal, the crystal in Crystalline Form 1 and the crystal in Crystalline Form 2) was added to soybean oil (200 μL), and the mixtures were transferred to a polypropylene vessel and mixed vigorously. Then, they were allowed to stand still at room temperature, and the time period until all of the crystals floating on the soybean oil were precipitated to the bottom of the vessel was measured, which was used as an index of dispersibility for each crystal.

The results are shown in Table 1.

TABLE 1

|  | Precipitation time (min) |
| --- | --- |
| Crystalline Form 1 | 30 |
| Crystalline Form 2 | 45 |
| Precursor crystal | 0.5 |

As shown in Table 1, for the precursor crystal, all of the crystals were precipitated to the bottom of the vessel in 0.5 minute, while the crystals in Crystalline Form 1 and Crystalline Form 2 required 30 minutes and 45 minutes to be precipitated, respectively. This indicated that the crystals in Crystalline Form 1 and Crystalline Form 2 had improved dispersibility in edible oils and fats over the precursor crystal. Table 1 shows that the dispersibility of the crystals in Crystalline Form 1 and Crystalline Form 2 in edible oils and fats was improved to be 50 times or more higher than that of the precursor crystal.

Typically, in producing soft capsules, an effective ingredient is mixed and formulated with edible oils and fats. The low water content PQQ disodium crystal according to the present invention has a higher degree of dispersibility than that of the conventional crystal, and is believed to be suitable for production of soft capsule formulations, for example.

Example 7

Permeability Test of PQQ Disodium Crystals in Crystalline Form 1 and Crystalline Form 2 Through Skin In this example, the PQQ disodium crystals in Crystalline Form 1 and Crystalline Form 2 prepared in Example 6 were compared to the precursor crystal in permeability through skin.

The PQQ disodium crystals in Crystalline Form 1 and Crystalline Form 2 prepared in Example 6 and the precursor crystal obtained in Reference Example 1 were each mixed with L-ascorbic acid powder (from Wako, special grade) in a weight ratio of 1:4 to prepare compositions for testing, and the compositions were used for permeability test. L-ascorbic acid powder was used as a control.

The permeability test was conducted using pig skin. The pig skin was washed with tap water, and the water was wiped out completely. This pig skin was brought to be in contact with each of the compositions for testing (5 mg), and then was fixed to the skin with tape. After 80 minutes, the tape was removed, and the skin was washed with tap water followed by removal of the compositions for testing adhered to the surface of the skin. The extent of permeability of the PQQ crystal to the skin was evaluated on the basis of the extent of coloring of the skin. Specifically, in this example, it was evaluated by capturing the photograph of the skin after the tests on a computer, and measuring the change in the brightness of the skin using an image-processing software (Product name: Paint (attached software in Windows XP), Microsoft Corp.). Here, the change in the brightness of the skin was calculated according to the following equation:

([The brightness of the untreated skin]−[The brightness of the treated skin])×100/[The brightness of the untreated skin]   [Equation 1]

The results are shown in Table 2.

TABLE 2

|  | Permeability through the skin |
|---|---|
| Crystalline Form 1 | 44 |
| Crystalline Form 2 | 59 |
| Precursor crystal | 32 |
| L-ascorbic acid powder | 0 |

As shown in Table 2, the crystals in Crystalline Form 1 and Crystalline Form 2 showed higher permeability through the skin compared with the precursor crystal. This indicated that the PQQ disodium crystals in Crystalline Form 1 and Crystalline Form 2 are more suitable for use in cosmetics and pharmaceuticals for percutaneous administration.

Prescription Example 1

Gelatin Capsule Formulation

Coenzyme Q10 (from MITSUBISHI GAS CHEMICAL COMPANY, INC.) (8 g), soybean protein hydrolysate (from Nisshin OilliO) (2 g), and the PQQ disodium crystal in Example 1 (Crystalline Form 1) (2 g) were added to a plastic bag, and were mixed by shaking the bag to prepare a composition for oral ingestion. The resulting composition was encapsulated 10 mg each in gelatin capsules to prepare gelatin capsule formulations.

Prescription Example 2

Oil Dispersion Soft Capsule Formulation

Safflower salad oil (from Nisshin OilliO) (2700 g), glycerin fatty acid ester (from RIKEN VITAMIN CO., LTD.) (300 g), and beeswax (from YOKOHAMA OILS & FATS INDUSTRY, CO., LTD.) (300 g) were mixed together and the resultant mixture was stirred at 70° C., and then the PQQ disodium crystal (Crystalline Form 1) in Example 1 was added to the mixture, and the mixture was mixed using a mixer. The resulting mixture was encapsulated in a soft capsule to prepare a soft capsule formulation.

The invention claimed is:

1. A pyrroloquinoline quinone disodium crystal, comprising:
    water at a content of 7% by weight or less, and
    a pyrroloquinoline quinone disodium crystal in Crystalline Form 1 or Crystalline Form 2,
    wherein
    the Crystalline Form 1 has 2θ angle peaks at 11.4±0.4, 13.5±0.4, 18.0±0.4, 18.7±0.4, 26.0±0.4, and 28.5±0.4° obtained by powder X-ray diffraction using a Cu Kα radiation, and
    the Crystalline Form 2 has 2θ angle peaks at 8.7±0.4, 11.5±0.4, 12.0±0.4, 17.4±0.4, and 18.7±0.4° obtained by powder X-ray diffraction using a Cu Kα radiation.

2. The pyrroloquinoline quinone disodium crystal according to claim 1, wherein the content of water is 4.6% by weight or less.

3. The pyrroloquinoline quinone disodium crystal according to claim 1, comprising the pyrroloquinoline quinone disodium crystal in the Crystalline Form 1.

4. The pyrroloquinoline quinone disodium crystal according to claim 1, comprising the pyrroloquinoline quinone disodium crystal in the Crystalline Form 2.

5. A pharmaceutical composition, comprising the pyrroloquinoline quinone disodium crystal according to claim 1.

6. A method for producing the pyrroloquinoline quinine disodium crystal, wherein the precursor crystal is a pyrroloquinoline quinine disodium crystal having 2θ angle peaks at 9.14-0.4, 10.3 0.4, 13.8±0.4, 17.7±0.4, 24.010.4, 27.4+0.4, and 39.5±0.4°obtained by powder X-ray diffraction using a Cu Ka radiation, and wherein the drying occurs by heating the precursor crystal in at least one oil according to claim 1, the method comprising drying a precursor crystal of the pyrroloquinoline quinine disodium crystal, wherein the precursor crystal is a pyrroloquinoline quinine disodium crystal having 2θ angle peaks at 9.14-0.4, 10.3 0.4, 13.8±0.4, 17.7±0.4, 24.010.4, 27.4+0.4, and 39.5±0.4°obtained by Powder X-ray diffraction using a Cu Ka radiation, and wherein the drying occurs by heating the precursor crystal in at least one oil to obtain the pyrroloquinoline quinine disodium crystal, wherein the precursor crystal is a pyrrolouininoline quinine disodium crystal having 2θ angle peaks at 9.14-0.4, 10.3 0.4, 13.8±0.4, 17.7±0.4, 24.010.4, 27.4+0.4, and 39.5±0.4°obtained by Powder X-ray diffraction using a Cu Ka radiation, and wherein the drying occurs by heating the precursor crystal in at least one oil.

7. The method according to claim 6, wherein the precursor crystal is crystallized by adjusting a pH of an aqueous solution comprising ethanol or isopropanol at a concentration of 10% to 90% in which a pyrroloquinoline quinone sodium salt is dissolved to a pH of from 2 to 5.

* * * * *